United States Patent [19]

Sugisawa et al.

[11] Patent Number: 4,690,699
[45] Date of Patent: Sep. 1, 1987

[54] APPARATUS FOR PRODUCING STERILE AIR

[75] Inventors: Ko Sugisawa, Nara; Kazuya Sekiguchi, Ikoma; Masao Taguchi, Osaka; Masayuki Nakatani, Higashiosaka; Hitoshi Iwata, Tsuzuki, all of Japan

[73] Assignee: House Food Industrial Co., Ltd., Osaka, Japan

[21] Appl. No.: 746,393

[22] Filed: Jun. 19, 1985

[30] Foreign Application Priority Data

Jun. 27, 1984 [JP] Japan ............................. 59-132200

[51] Int. Cl.$^4$ ............................................ B01D 46/00
[52] U.S. Cl. .................................... 55/267; 55/279; 55/97; 422/109; 422/292; 137/597
[58] Field of Search ............................ 55/97, 267–269, 55/279; 422/26, 292, 293, 109; 137/597; 251/122

[56] References Cited

U.S. PATENT DOCUMENTS

| | | | |
|---|---|---|---|
| 3,881,896 | 5/1975 | Rothmayr et al. | 55/97 |
| 4,099,703 | 7/1978 | Lush | 251/122 |
| 4,241,020 | 12/1980 | Grantham | 422/292 |
| 4,435,194 | 3/1984 | Picard et al. | 55/96 |
| 4,489,721 | 12/1984 | Ozaki et al. | 137/597 |
| 4,547,339 | 10/1985 | McClure | 422/26 |

Primary Examiner—Bernard Nozick
Attorney, Agent, or Firm—Harry M. Weiss & Associates

[57] ABSTRACT

An apparatus for producing sterile air comprises a sterilizing filter for filtering microbes in air and an air heater for heating the filtered air for its sterilization. There is provided means for disposing of the sterile air from the air heater at an initial stage of production of the sterile air.

3 Claims, 3 Drawing Figures

APPARATUS FOR PRODUCING STERILE AIR

FIELD OF THE INVENTION

This invention relates to an apparatus for producing sterile air completely and safely, the sterile air being required for storing in an aseptic tank products sterilized in an aseptic condition so as to maintain their sterile state.

DESCRIPTION OF THE PRIOR ART

Sterile air is generally used for keeping a sterilized product in an aseptic tank in its sterile state before aseptic filling. That is, the sterile air is used for the purpose of preventing penetration of the ambient air into the aseptic tank by keeping the pressure within the aseptic tank higher than the atmospheric pressure outside the tank. This sterile air is produced by filtering microbes floating in the air through a sterilizing filter. In this case, the sterilizing filter is usually subjected to steam sterilization in advance for the purpose of extinction of those microbes which are caught by the sterilizing filter before and those which subsequently adhere to the filter after its use. However, this steam sterilization has disadvantages in that it damages the sterilizing filter to reduce its microbe capture effect and even a sterilizing filter having a high microbe capture effect gradually experiences a reduction in that effect.

The inventors intended to solve the above problem, which is experienced with sterilizing filters, by use of a sterilizing filter together with an air heater. However, the mere use of a sterilizing filter together with an electrical air heater developed the following defects. First, when the sterilizing filter and the electrical air heater are subjected to steam sterilization, the condensate of steam wets the electrical heater element, which may develop short circuits due to the condensate when the heater element is energized for production of sterile air, whereby excess current flows and destroys the heater element. Secondly, when the steam remaining in the aseptic tank is replaced by sterile air produced by an sterile air producting apparatus and supplied into the aseptic tank after the steam sterilization of the sterile air producing apparatus, the pressure within the aseptic tank tends to become negative because of condensation of the steam. A large amount of aseptic air, therefore, is hastily required in order to maintain the high pressure within the aseptic tank. At this time, the air heater can hardly respond to a change in the air stream in the sterile air producing apparatus from the state in which only a slight amount of air is flowing to one in which a large quantity of air starts to flow, whereby the temperature of the air heater is reduced to such a degree that the temperature necessary for sterilization can not be maintained.

SUMMARY OF THE INVENTION

Accordingly it is an object of the invention to eliminate the above-described defects and to provide an apparatus for producing sterile air completely and safely and which is capable of steadily supplying the sterile air to an aseptic tank immediately after sterilization treatment of the tank at a rate which is sufficient to maintain the high pressure in that tank.

To achieve this aim, this invention provides an apparatus for producing sterile air comprising: an air supply pipe having a sterilizing filter for filtering microbes in air; an sterile air supply pipe having a shutoff valve; an air heater which is provided between said air supply pipe and said sterile air supply pipe; and an air or condensate discharging pipe having a discharge valve at least on the upstream of said shut-off valve, the latter being closed to discharge sterile air from the air heater through said discharge valve at an initial stage of production of the sterile air.

Additional features and objects of the invention will become apparent from the following description in which the preferred embodiment thereof is set forth with reference to the accompanying drawings.

Figure 1:
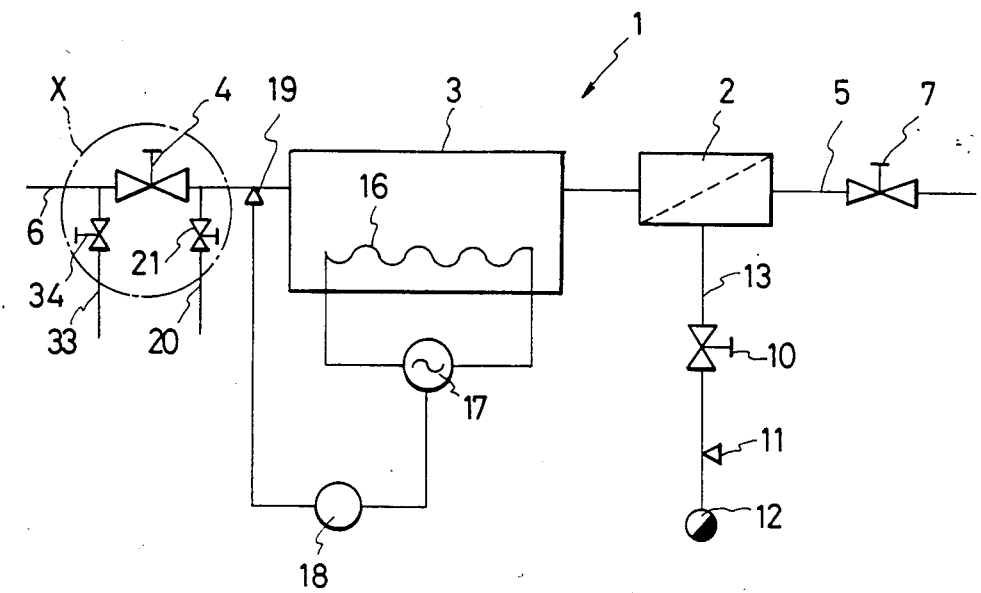
FIG. 1 shows an embodiment of an apparatus for producing sterile air according to the invention.

In the drawings, there is shown a sterile air producing apparatus indicated by reference numeral 1 and comprising a sterilizing filter 2 provided in an air supply pipe 5, an air heater 3 connected to one end of the air supply pipe 5, and a shut-off valve provided in an sterile air supply pipe 6 which extends from the air heater 3. A compressor 8 is connected to the other end of the air supply pipe 5 through a compressed air supply valve 7, and a aseptic tank 9 is connected to the other end of the sterile air supply pipe 6. A valve 10, a temperature sensor 11, and a stream trap 12 are provided in a pipe 13 extending from the sterilizing filter 2. A steam valve 14 is connected to a steam supply pipe 15 to control a flow rate of the steam supplied therefrom depending upon temperature of the steam in the pipe 13 which is detected by the temperature sensor 11. There are no special limitations with regard to the type of air heater employed, but the electrical heating type is preferable from the viewpoint of facilitating temperature control. In this case, the air heater 3 is provided with a heater element 16, a transformer 17 for the heater element 16 and a temperature controller 18. The temperature controller 18 is connected to a temperature sensor 19 which is provided in the sterile air supply pipe 6 to detect the temperature of the interior of the air heater 3.

Figure 3:
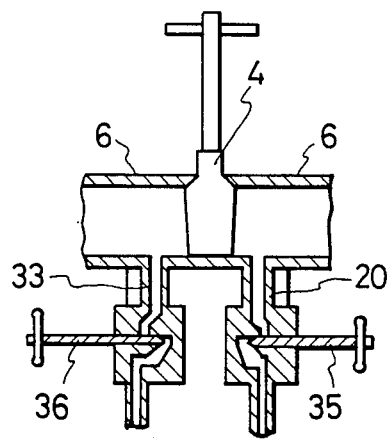

An air or condensate discharge pipe 20 and a pipe 33 are connected to the sterile air supply pipe 6 on the upstream and downstream sides, respectively, of the shutoff valve 4, as is shown in FIG. 1, and are provided with discharge valves 21 and 34, respectively, which may be in the form of needle valves 35, 36, and is shown in FIG. 3, from the viewpoint of facilitating flow rate control.

Figure 2:
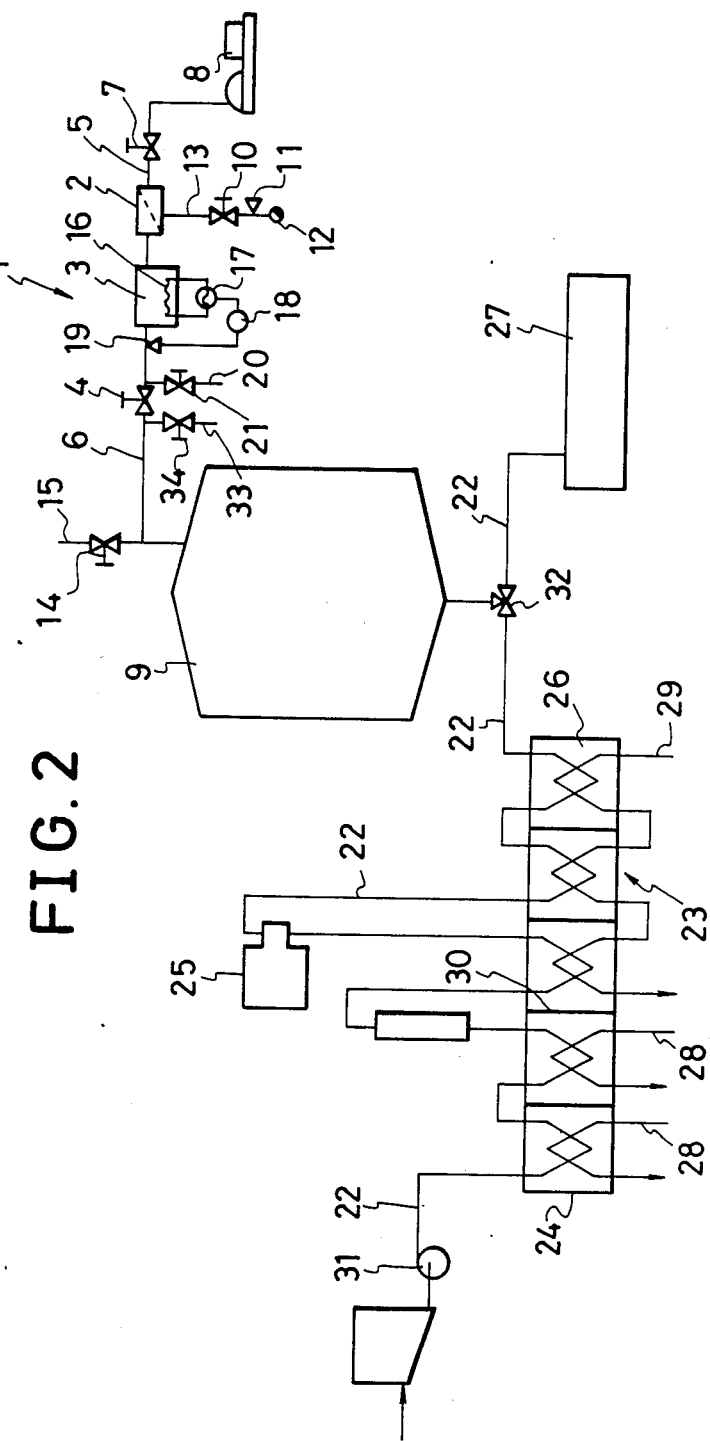
FIG. 2 shows an embodiment of an aseptic product producing plant with the sterile air producing apparatus shown in FIG. 1 installed therein and, FIG. 3 is a cross-sectional view of valves showing in detail a portion indicted by X in FIG. 1.

An embodiment of an aseptic product producing plant with an sterile air producing apparatus according to the invention installed therein will be explained in the following with reference to FIG. 2.

A heat exchanger 23 has a heater section 24 and a cooler section 26 which are separated by a partition plate 30 and interconnected by a product pipe 22 having a homogenizer 25 outside the heat exchanger 23. The product pipe 22 is connected to an aseptic filling machine 27. The aseptic tank 9 is connected to the product pipe 22 through a three-way type valve 32 between the cooler section 26 and the filling machine 27. Steam pipes 28 are provided within the heater section 24 of the heat exchanger 23 to heat the product which flows through the product pipe 22, and, on the other hand, a cooling water pipe 29 is provided within the cooler section 26 of the heat exchanger 23 to cool the product heated in the heater section 24.

At the first stage a pump 31 is used to feed water into the product pipe 22 and water is heated in the heater section 24 in order to sterilize the inside of the product pipe 22 by hot water flowing through the pipe 22. In this case, the three-way type valve 32 is controlled in advance so as to be capable of passing the flow of the hot water through the product pipe 22 to the aseptic filling machine 27.

Apart from the sterilization of the product pipe 22, the sterile air producing apparatus 1 and the aseptic tank 9 are subjected to steam sterilization. The valve 7 is first closed and the valve 14 and the shut-off valve 4 are opened to supply the steam from the steam supplying pipe 15 to the sterile air producing apparatus 1 and the aseptic tank 9 through the sterile air supply pipe 6. While the steam is being supplied, the discharge valve 21 is kept open. The air heater 3 and the sterilizing filter 2 are sterilized by steam passing through them, and subsequently the steam passes through the pipe 13 and the valve 10 to the steam trap 12, where condensate of the steam is discharged. At that time, the temperature sensor 11 provided in the pipe 13 detects the steam temperature within the pipe 13 and sends signals to the valve 14 for controlling the flow rate of the steam from the steam supplying pipe 15 whereby the temperature of the interior of the sterile air producing apparatus 1 and the tank 9 is controlled to be appropriate for sterilization, usually about 130° C.

After sterilization of the whole of the aseptic tank 9 and the sterile air producing apparatus 1, the shut-off valve 4 and the valve 10 are closed while the valve 14 remains open, and then, the valve 7 is opened. The valve 34 is opened to discharge the steam existing in the sterile air supply pipe 6 together with the steam supplied from the steam supplying pipe 15. This operation can prevent the reduction of sterilization temperature in the tank and the pipe 6 which may be caused by the accumulating condensate of the steam.

The compressed air from the compressor 8 which has been operated in advance is next supplied to the sterile air producing apparatus 1. The compressed air supplied is filtered through the sterilizing filter 2, and then is supplied to the air heater 3. At this stage, the air heater 3 is not in operation. After the water in the air heater 3 together with the compressed air therein is drained out through the air or condensate discharge pipe 20 and the air heater 3 is adequately dried, the heater element 16 of the air heater 3 is energized to heat the compressed air which passes through the air heater 3. The temperature sensor 19 provided in the sterile air supply pipe 6 on the outlet side of the air heater 3 detects the temperature of the compressed air which has been heated by the heater element 16 and sends the signals to the temperature controller 18. The temperature controller 18 electrically controls the heater element 16 through the transformer 17 so that the compressed air is heated to any temperature within the range of about 250° C. to 450° C. appropriate for sterilization. The compressed air (sterile air) which has been heated and sterilized is discharged from the air or condensate discharge pipe 20 through the discharge valve 21 until the flow rate of the sterile air from the air heater 3 reaches at a predetermined value.

Then, the valve 14 is closed to stop the supply of the steam and the discharge valve 21 is next closed and at the same time the shut-off valve 4 is opened to introduce the sterile air into the aseptic tank 9. The supply of the sterile air is conducted so that the steam in the aseptic tank 9 is replaced by the sterile air to keep the aseptic tank 9 in pressurized state. The steam condensed in the aseptic tank 9 passes from the bottom of the aseptic tank 9 through the three-way type valve 32 to the product pipe 22 from which the condensed steam is discharged through the filing machine 27.

According to the invention, there is provided an apparatus comprising a sterilizing filter and an air heater which can achieve a complete and safe sterilization of the compressed air. In this apparatus, steam is utilized to sterilize the sterilizing filter and the air heater before production of sterile air, and then, air is used to dry the interior of the air heater, and thereafter compressed air is filtered and heated for its sterilization. This structure is able to avoid any trouble which would occur in the air heater as a result of its short circuiting due to the presence of condensate. Further, in this apparatus, the sterile air is not supplied to an aseptic tank until the flow rate and temperature of the sterile air from the air heater 3 reaches at a predetermined value.

Therefore, the tank is supplied with sterile air from the air heater in its stable state where the air heater is maintained at the temperture necessary for sterilization of air.

The above description is included to illustrate the operation of the preferred embodiment and is not intended to limit the scope of the invention. The scope of the invention is to be limited only by the following claims. From the above description, many variations will be apparent to one skilled in the art that would yet be encompassed by the spirit and scope of the invention.

We claim:

1. An apparatus for producing sterile air, comprising:
   a compressor;
   an air supply pipe connecting a sterilizing filter for filtering microbes to said compressor and disposed downstream therefrom;
   a connecting pipe connecting said sterilizing filter to an air heater disposed downstream from said sterilizing filter; a sterile air supply pipe connecting said air heater to a downstream aseptic tank, said sterile air supply pipe further having a shut-off valve; and
   an air or condensate discharging pipe having a discharge valve at least on the upstream side of said shut-off valve, said shutt-off valve being closed to discharge sterile air from said air heater through the discharge valve at an initial stage of the production of the sterile air.

2. An apparatus for producing sterile air according to claim 1, wherein said air heater is an electrical air heater.

3. An apparatus for producing sterile air according to claim 1, wherein said discharge valve is a needle valve.

* * * * *